United States Patent [19]
Seidel et al.

[11] 4,409,076
[45] Oct. 11, 1983

[54] INDIRECT ELECTROCHEMICAL FURAN SYNTHESIS

[75] Inventors: William C. Seidel, Hockessin; Dimitri N. Staikos, Wilmington, both of Del.

[73] Assignee: E. I. Du Pont de Nemours & Company, Wilmington, Del.

[21] Appl. No.: 347,730

[22] Filed: Feb. 10, 1982

[51] Int. Cl.³ .............................................. C25B 3/02
[52] U.S. Cl. ..................................... 204/130; 204/78
[58] Field of Search .................................. 204/78–80, 204/130

[56] References Cited

U.S. PATENT DOCUMENTS 2,964,453 12/1960 Garn et al. ........................... 204/130
3,413,203 11/1968 MacLean .............................. 204/79
3,745,180 7/1973 Rennie ................................. 204/78
3,776,824 12/1973 Bernstein et al. ..................... 204/78
4,264,678 5/1981 Faul et al. ........................... 204/130

Primary Examiner—R. L. Andrews

[57] ABSTRACT

Process for preparing a furan compound by oxidizing a diolefin, using copper as the oxidizing agent, and regenerating spent copper by electrolytic oxidation.

16 Claims, No Drawings ously known. In particular, U.S. Pat. No. 4,172,838 discloses

INDIRECT ELECTROCHEMICAL FURAN SYNTHESIS

FIELD OF THE INVENTION

This invention relates to processes for the preparation of furan compounds from diolefins, and more particularly to processes which include electrolytic regeneration of catalysts useful in the processes.

BACKGROUND INFORMATION

Furan is a chemical useful in furan resins, but more importantly, it serves as an intermediate for the manufacture of tetrahydrofuran and 1,4-butanediol. Processes for indirect oxidation of butadiene to furan are known. In particular, U.S. Pat. No. 4,172,838 discloses a process for the preparation of furan compounds by catalytic oxidation of a diolefin such as butadiene in an aqueous medium having a pH less than 2 and containing iodide ion, a mixture of cuprous and cupric ions, and a solubilizing agent for cuprous ion such as an alkali metal halide. Regeneration of the cupric ion oxidant is achieved by oxidation of cuprous ion with an oxygen-containing gas and may be carried out by mixing an oxygen-containing gas directly with the diene starting material, or in the second stage of a two-stage process.

S. Torii, Catalyst (Japan), 22, 330–341 (1980), reviews indirect electrolytic oxidation in organic syntheses, that is oxidation which takes place in the bulk solution away from the electrodes using a redox reactant which aids electron transfer in a homogeneous system. In such a system an oxidizing electron carrier is employed as an intermediary between the substrate and the electrodes. First, the oxidizing electron carrier oxidizes the substrate, and then the reduced electron carrier is oxidized at the anode to provide oxidation activity again. This cycle is used for repeated oxidation of the substrate. Thus the indirect electrolytic oxidation process involves the oxidation of a substrate by electrolysis, not directly, but by the regeneration and recirculation of the oxidizing electron carrier.

An example of a commercial application of the technology is the ECRU SYSTEM for chromic acid regeneration manufactured by Resource Engineering Company. This system is designed for electrolytic regeneration of chromium oxidizing solutions, e.g., plastic etches, brass and aluminum bright dyes, anodizing solutions and organic oxidants, by generating chromic acid from chromium (III).

DISCLOSURE OF THE INVENTION

The invention resides in a process for preparing a furan compound by indirect electrochemical synthesis. In particular, the invention resides in an improved process for preparing a furan compound by oxidizing a diolefin in the presence of copper having an average oxidation state between 1 and 2, wherein the improvement comprises regenerating spent copper by electrolytic oxidation.

In the process of the invention, a diolefin is oxidized to a furan compound as, e.g., disclosed in U.S. Pat. No. 4,172,838, i.e., in the presence of a catalyst system comprising a mixture of cuprous and cupric ions, iodine and a solubilizing agent for the cuprous ions in an aqueous medium. The cuprous ions, or spent copper, are oxidized, or regenerated, by electrolytic oxidation as further described below.

Regeneration of spent copper by electrolytic oxidation is an improvement in said oxidation of a diolefin to a furan compound in that (1) the $Cu^{+2}$ ion concentration can be maintained much closer to its optimum level by continuous electrochemical reoxidation; (2) the overall process can be more satisfactorily carried out in a single reactor which combines diene absorption and copper ion reoxidation; (3) the co-product hydrogen evolved from the cathode compartment of the electrolytic cell can be usefully employed in chemical syntheses, e.g., for hydrogenation of furan to tetrahydrofuran.

The improved process of the invention comprises several embodiments. For example, the process may be carried out in multiple stages or vessels or in a single stage or vessel. A multiple vessel process may include diene absorption in a first vessel, oxidation of intermediates to furan in a second vessel and regeneration of spent catalyst in a third vessel. Electrolytic oxidation of spent catalyst may occur in one or more of the vessels; regeneration in the third vessel may be effected chemically (e.g., by oxygen as disclosed in U.S. Pat. No. 4,172,838), or electrochemically. A two-vessel oxygen regeneration process is disclosed in U.S. Pat. No. 4,172,838. A single vessel process has several advantages including necessity of fewer components and reduced danger from circulating carcinogenic intermediates, i.e., intermediate products of diene reaction with copper halides such as dichlorobutenes. A possible disadvantage is difficulty in separating products from a single vessel. The following description is primarily directed to a single vessel process. A variety of multiple vessel embodiments will be obvious to persons skilled in the art based on the description provided.

Useful diolefins which can be employed as starting materials in the process of the invention have the formula $RCH=C(R^1)C(R^2)=CHR$ wherein R, $R^1$ and $R^2$ are selected from hydrogen or an alkyl group of 1 to 4 carbon atoms with the proviso that the total number of carbon atoms in the diolefin does not exceed 8. Examples include 1,3-butadiene; 1,3-pentadiene; 2-methyl-1,3-butadiene (isoprene); 1,3-hexadiene; 2,4-hexadiene; 2,3-dimethyl-1,3-butadiene; 3,4-dimethyl-2,4-hexadiene; 4,6-octadiene; and 1,3-octadiene. Of the exemplary diolefins, the first three are preferred because of commercial availability, with 1,3-butadiene being especially preferred. Mixtures of diolefins can be used if desired.

When used in the process of the invention, the diolefin can be used undiluted or mixed with a gas inert to the reaction, such as nitrogen, carbon monoxide, oxygen or carbon dioxide. When oxygen is employed it is desirable to operate outside the explosive limits of diolefin/oxygen mixtures.

It is preferred that water be the only solvent in the aqueous medium. However, other aqueous solutions in which water is diluted with hydrophilic solvents, e.g., acetic acid, sulfolane, acetonitrile and dioxane may also be used as may aqueous solutions in which an organic solvent is used as a cuprous ion solubilizing agent as discussed below. The amount of water in the aqueous medium should be at least about 20 moles per liter.

Any iodine-containing compound which is at least partially soluble in the aqueous medium can be used. Illustrative iodine-containing compounds are lithium iodide, calcium iodide, cuprous iodide, ferrous iodide, potassium iodide, hydriodic acid and organic iodides such as methyl iodide and ethyl iodide. Of these, iodine from elemental iodine or alkali metal iodides, especially sodium iodide and potassium iodide, are preferred. The concentration of iodine in the aqueous medium will normally be in the range of about $1 \times 10^{-6}$ to 0.1 gram mole per liter, preferably in the range of about 0.001 to 0.05 gram-mole per liter. The iodine is believed to be in the form of iodide ion in the aqueous medium.

Any copper compound soluble in the aqueous medium can be used, although copper halides such as the chlorides and bromides are preferred. Especially preferred is a mixture of cupric chloride and cuprous chloride although either one alone can be added to the aqueous medium, in which event a mixture of the two copper ions is quickly obtained by oxidation or reduction. The total copper concentration in the aqueous medium will usually be in the range of about 0.1 to 10 gram-moles per liter, and normally about 0.5 to 3 gram-moles per liter. Under preferred operating conditions, with chloride ions, there will be an initial ratio of cupric ion to cuprous ion of 100:1 to 1:2. The ratio will remain substantially constant as the oxidation proceeds since cupric ion is continuously regenerated. Illustrative copper compounds that can be used are halides of copper such as cupric chloride, cupric bromide, cuprous chloride, cuprous bromide and cuprous iodide; copper salts of organic acids, which may be carboxylic acids, such as acetic, propionic, pivalic, formic, succinic or adipic acids, fluorinated carboxylic acids, such as trifluoroacetic acid, sulfonic acids, such as methanesulfonic acid, benzenesulfonic acid and p-toluenesulfonic acid or fluorinated sulfonic acids, such as trifluoromethylsulfonic acid; salts of inorganic acids, such as cupric sulfate, cupric nitrate and cupric tetrafluoroborate; and cupric cyanide.

A solubilizing agent is used to keep cuprous ions in solution. Useful solubilizing agents include any inorganic or organic compound which is soluble in water and tends to form a water-soluble complex with cuprous ion. Alkali metal halides, alkaline earth metal halides, ammonium halides and halogen acids are preferred, but other metal halides such as palladium halides and iron halides, and organic solvents can also be used. Useful halides are the chlorides and bromides, preferably the chlorides. Illustrative organic compounds are (1) organic nitriles including aliphatic nitriles such as acetonitrile, succinonitrile, and propionitrile and aromatic nitriles such as benzonitrile; (2) carboxylic acids such as acetic acid; (3) thiocyanates such as sodium thiocyanate; and (4) aromatic amines or their hydrochlorides such as tetramethylethylenediamine. It is within the skill of the art to select a particular solubilizing agent and the appropriate amount to use. Especially preferred solubilizing agents are sodium chloride, calcium chloride and ammonium chloride. The concentration of the solubilizing agent is typically in the range of about 0.01 to 5 gram-moles per liter, preferably about 0.5 to 4 gram-moles per liter.

The process of the invention may be conveniently carried out in an electrolysis cell in which the anode and cathode compartments are separated. In such a cell, oxidation of a diolefin will occur primarily in the anode compartment. Because of the corrosive nature of the copper salt solution, suitable materials of cell construction include glass, ceramic-lined metals, titanium, titanium-clad metals, and the like. A suitable inert membrane for separation of the anode and cathode compartments is a perfluorinated polymeric sulfonic acid. Preferred as anode and cathode materials are platinum, platinum-coated metals, and carbon.

For efficient oxidation of the diolefin, the aqueous medium should have a pH less than about 2, as measured by any known type of pH measuring device. It is preferred that the pH be less than about 0.5. The molarity of the hydrogen ion will preferably be at least about 0.05, most preferably in the range of about 0.1 to 1.0.

Measurement of pH by glass electrodes in the aqueous solutions of copper salts which are used in the process of the invention does not accurately measure the molar concentrations of hydrogen ion. For example, the pH of a solution which is 0.1 normal in hydrochloric acid and contains the concentrations of copper salts which are exemplified, is below 0 when measured with a glass electrode. The molar concentrations of hydrogen ions in the mixes may be determined by titrations of aliquot samples dissolved in 10-fold quantities of water with standard base solutions. Standard techniques for determining the end-points of acid-base titrations may be used, i.e., by indicators, such as Congo Red or Methyl Orange, or with a pH meter.

The process of the invention can be carried out at temperatures of about 50°–125° C., and preferably in a temperature range of about 95°–110° C. As would be expected, rates of furan production are reduced at lower temperatures. Reaction pressures are conveniently in the range of about 1–10 atmospheres (0.1–1.0 MPa), and preferably about 1 atmosphere (0.1 MPa).

It is preferred that the aqueous medium be agitated, either mechanically or by gas dispersion in the medium, and that the reaction off-gases containing furan product be removed from the anode compartment promptly. The optimum contact time between the diolefin starting material and the aqueous medium depends on a number of factors and is readily determined by one skilled in the art.

The electrolytic oxidation should be carried out in a preferred oxidation potential range to maximize the rate of reaction and the yield of furan. For example, as the oxidation potential of the system is decreased below about 400 millivolts, furan yield is increased but the conversion rate of diolefin to furan is decreased. Oxidation potentials greater than about 435 millivolts are unsatisfactory due, it is believed, to oxidation of iodide ion to iodine at these higher potentials. It is preferred to operate at an oxidation potential of about 380 to 410 millivolts.

In a preferred embodiment of the process, 1,3-butadiene is converted to furan by reaction in a solution which is initially about 0.3 molar in hydrogen ion (from hydrochloric acid), 1.0 molar in cupric chloride, 1.5 molar in cuprous chloride, 0.02 molar in iodide ion (from potassium iodide), and 3.0 molar in excess chloride ion as ammonium chloride or sodium chloride.

EXAMPLES

The following are illustrative examples of the process of the invention in which all parts and percentages are by weight and all degrees are Celsius unless otherwise noted. The conversions reported are calculated by the formula:

$$\% \text{ conversion} = \frac{\text{moles diolefin consumed}}{\text{moles diolefin charged}} \times 100$$

The furan yield is the mole percent of product which is furan.

EXAMPLE 1

A glass electrochemical cell with two compartments separated by a perfluorinated polymeric sulfonic acid membrane was employed. The anode compartment was equipped with a gas-inlet dip tube, high speed stirrer, platinum wire connected to a standard Calomel electrode, and gas outlet tube, vented through a condenser. The cathode compartment was equipped with a gas outlet tube for the hydrogen gas generated. Platinum wire electrodes were employed for the anode and cathode. The anode compartment was charged with 30 g of cupric chloride, 10 g of cuprous chloride, and 12.83 g of ammonium chloride. Distilled water and 3 ml of concentrated hydrochloric acid were added to a total volume of 100 ml. The reactor was heated to 100° and the oxidation potential of the medium was adjusted to 0.430 volt vs. the standard Calomel electrode. An electrolyte solution was prepared by dissolving 12 g of ammonium chloride in a solution of 100 ml of water and 3 ml of concentrated hydrochloric acid and this solution was charged to the cathode compartment. A standardized mixture of 10% butadiene and 90% nitrogen, by volume, was charged to the reactor through the dip tube. After 5 minutes, 0.66 g of sodium iodide was added and current was applied to the cell. The average current requirement was 0.3 amp. Aqueous sodium hydroxide (50%) was injected into the reactor to maintain a constant acidity. At 0.3 amp current consumption, 0.67 ml/hour of sodium hydroxide was required.

In this example, the potential was maintained at 0.430 volt for 3 hours and then decreased to 0.415 volt for an additional 3 hours. The average hydrogen ion concentration was 0.25 M. During the operation at 0.415 volt the furan yield was 90% at 18% butadiene conversion. Furan was identified by mass spectral analysis.

EXAMPLE 2

The anode compartment of the electrochemical cell of Example 1 was charged with 125 ml of a catalyst solution containing 1.3 moles/L of cupric chloride, 1.5 moles/L of cuprous chloride, 0.7 mole/L of hydrochloric acid and 0.05 mole/L of potassium iodide. The cathode compartment was charged with 5% aqueous hydrochloric acid. Gaseous butadiene, mixed with nitrogen, was charged through the dip tube at a rate of 0.22 g of butadiene/hour; the nitrogen flow rate was 20 ml/min, and the butadiene flow rate was 2 ml/min. The cell was heated to 100°. Current was applied and the potential was adjusted to 0.425 volt. Furan was produced at a 23% yield with 36% conversion of butadiene charged. The furan was identified by gas chromatography on a T. M. Waters Assoc. Porpak® N column at 180°, 25 ml/min helium flow and by mass spectroscopy.

EXAMPLE 3

The anode compartment of the electrochemical cell of Example 1 was charged with 40 g of cupric chloride, 28 g of cuprous chloride, 30 g of ammonium chloride, 1.25 g of sodium iodide, and 8 ml of concentrated hydrochloric acid. Water was added to a total volume of 200 ml. An electrolyte solution was prepared by dissolving 12 g of ammonium chloride in a solution of 100 ml of water and 3 ml of concentrated hydrochloric acid, and this solution was charged to the cathode compartment. The reactor was heated to 95°, and nitrogen was admitted through the dip tube at 40 ml/min. Isoprene was pumped at 1.0 ml/hour into the nitrogen feed gas subsurface to the catalyst solution. The oxidation potential of the reactor was maintained at 0.400 volt using 1.0 amp current. The acid concentration was maintained at 0.3 M by addition of concentrated ammonium hydroxide at 1.9 ml/hour. 3-Methylfuran was identified in the off-gas of the reactor by gas chromatography.

EXAMPLE 4

The anode compartment of the electrochemical cell of Example 1 was charged with 29 g of cuprous bromide, 75 g of ammonium bromide, 2 g of cupric bromide, 0.5 g of iodine and 5 ml of hydrobromic acid. The reactor was heated to 95°, and the oxidation potential of the medium was adjusted to 0.390 volt using a standard Calomel electrode. An electrolyte solution was prepared by dissolving 12 g of ammonium bromide in a solution of 100 ml of water and 3 ml of concentrated hydrochloric acid, and this solution was charged to the cathode compartment.

A standard mixture of 10% butadiene and 90% nitrogen, by volume, was admitted to the reactor through a dip tube at the rate of 50 ml/min. The average current requirement was 1.2 amp. After 8 hours of operation, the butadiene conversion was 60% (3 ml/min) and the furan yield was 67%.

EXAMPLE 5

This example illustrates one embodiment of a multiple vessel process of the invention. Butadiene absorption was carried out in a first vessel, oxidation to furan in a second vessel, and regeneration of spent catalyst in a third vessel. Regeneration was effected both chemically and electrochemically. Oxygen was bubbled through the third reactor to carry out the chemical oxidation; an electrochemical cell, as described in Example 1, was attached to the third vessel to carry out the electrochemical oxidation. The first and third reactors were stirred during the process.

To each of the three reactors was charged 200 mL of an aqueous solution containing 2.0 moles/L of cuprous chloride, 1.2 moles/L of cupric chloride, 3.0 moles/L of ammonium chloride and 0.02 mole/L of sodium iodide. The reactors were heated to 95° and oxygen addition was started along with pumps which caused solution from the first reactor to flow into the second and third reactors and from the second and third reactors to the first reactor. When the entire catalyst solution was oxidized to the desired chemical potential, butadiene addition to the first reactor was started. Butadiene addition, along with reoxidation of the spent copper, electrochemically, and with oxygen, was carried out for one hour while the solution was flowed through the three reactors. During this period the pH of the catalyst solution was maintained at the buffered cupric hydroxide value of 4.5 to prevent oxidation to furan. Hydrochloric acid was next added to the furan reactor to give a concentration of 0.2 mole/L. Furan evolution began immediately. The potential of the three reactors was 397 mV, 405 mV and 409 mV, respectively. By controlling the pump speeds and butadiene and oxygen flow rates, the furan reactor was maintained acidic, about 0.2 mole/L, while the butadiene absorber and catalyst reoxidation reactors were maintained at pH 4.5. The reaction was carried out for 12 hours. Furan was produced in 62% yield with 36% butadiene conversion.

BEST MODE FOR CARRYING OUT THE INVENTION

The best mode contemplated by the applicants for carrying out the invention is described by Example 1, modified, where necessary, by the preferences indicated in the specification.

We claim:

1. Improved process for preparing a furan compound by oxidizing a diolefin in the presence of copper having an average oxidation state between 1 and 2, wherein the improvement comprises regenerating spent copper by electrolytic oxidation.

2. Process of claim 1 in which the diolefin has the formula $RCH=C(R^1)C(R^2)=CHR$ wherein R, $R^1$ and $R^2$ are selected from hydrogen or an alkyl group of 1 to 4 carbon atoms with the proviso that the total number of carbon atoms in the diolefin does not exceed 8.

3. Process of claim 2 in which the oxidation of the diolefin is carried out in an aqueous medium having a pH less than 2 in the presence of iodine and a solubilizing agent.

4. Process of claim 3 in which the process is carried out in multiple vessels.

5. Process of claim 3 in which diene absorption is carried out in a first vessel, oxidation of intermediates to furan in a second vessel, and regeneration of spent catalyst in a third vessel, electrolytic regeneration occurring in at least one vessel.

6. Process of claim 3 in which the process is carried out in a single vessel.

7. Process of claim 3 in which the electrolytic oxidation is carried out at 380 to 410 mV.

8. Process of claim 7 in which the aqueous medium includes at least 20 moles/liter of water.

9. Process of claim 7 in which the electrolytic oxidation is carried out using platinum, platinum-coated metals or carbon as anode and cathode materials.

10. Process of claim 7 in which the hydrogen ion concentration is at least 0.05 molar and the iodine concentration is about $1 \times 10^{-6}$ to 0.1 gram-mole per liter.

11. Process of claim 7 in which the temperature is 50° to 125° C.

12. Process of claim 7 in which the medium is agitated.

13. Process of claim 7 in which the pH is less than 0.5, the hydrogen ion concentration is 0.1 to 1.0 molar, the temperature is 95° to 110° C., the total copper concentration is about 0.1 to 10 gram-moles per liter and the initial ratio of cuprous to cuprous ions is 100:1 to 1:2.

14. Process of claim 7 or 13 in which the diolefin is 1,3-butadiene, 1,3-pentadiene or 2-methyl-1,3-butadiene.

15. Process of claim 13 in which the diolefin is 1,3-butadiene, the hydrogen ion source is hydrochloric acid, the initial hydrogen ion concentration is 0.3 molar, the initial cupric chloride concentration is 1.0 molar, the initial cuprous chloride concentration is 1.5 M, the iodide ion source is potassium iodide, the initial iodide ion concentration is 0.02 molar, the solubilizing agent is $NH_4Cl$ or NaCl and the chloride ion concentration from the solubilizing agent is 3.0 molar.

16. Process of claim 14 in which the solubilizing agent is NaCl, $CaCl_2$ or $NH_4Cl$ and the concentration of solubilizing agent is 0.5 to 4.0 gram-moles per liter.

* * * * *